United States Patent [19]
Yonemaru et al.

[11] Patent Number: 6,140,561
[45] Date of Patent: *Oct. 31, 2000

[54] TOMA-P

[76] Inventors: Akira Yonemaru, 2-33 Kinugasashita, Yokosuka, Kanagawa 238, Japan; Lulu Wakamiya, 15-K Legaspi Towers 300, Roxas Blvd., Pasay City, Metro Manila, Philippines

[ * ] Notice: This patent is subject to a terminal disclaimer.

[21] Appl. No.: 09/130,725

[22] Filed: Aug. 7, 1998

[51] Int. Cl.[7] .............................. A01H 5/00; A01H 5/10; A01H 4/00; C12N 5/04
[52] U.S. Cl. .................. 800/317; 800/317.1; 800/317.4; 435/410; 435/411; 435/423; 435/430
[58] Field of Search .................................. 800/317, 317.1, 800/317.4, 260, 269, 298; Plt./261, 258; 435/410, 422, 423, 430

[56] References Cited

PUBLICATIONS

Greenleaf. Chapter 3, Pepper Breeding. In: Breeding Vegetable Crops, Ed. Bassett. Avi Publishing Company, Inc. Connecticut. (excerpt, pp. 72–74), 1986.
Deloire et al. Annals of Botany. vol. 49, pp. 887–891, 1982.
Huxley, Ed. The New Royal Horticultural Society Dictionary of Gardening, The Stockton Press, New York. p. 869, 1992.
Livingstone et al. Genetics. vol. 152, pp. 1183–1202, 1999.
Palmer et al. Proceedings of the National Academy of Science. vol. 79, pp. 5006–5010, 1982.
Rick. Biosystematic studies in Lycopersicon and closely related species of Solanum. In: the Biology and Taxonomy of the Solanceae, Linnaen Society Symposium Series, No. 7, Academic, New York, 1979.
Samoylov et al. Theoretical and Applied Genetics. vol. 92, pp. 850–857, 1996.
Tigchelaar. Chapter 4, Tomato Breeding. In: Breeding Vegetable Crops, Ed. Bassett. Avi Publishing Company, Inc. Connecticutt. (excerpt, pp. 139–140,) 1986.

*Primary Examiner*—Gary Benzion
*Assistant Examiner*—Melissa L. Kimball
*Attorney, Agent, or Firm*—Rothwell, Figg, Ernst & Manbeck

[57] ABSTRACT

A new and distinct plant, Toma-P, fruit of said plant which has a crunchy texture but mild flavor, is described and claimed.

8 Claims, No Drawings

TOMA-P

BACKGROUND OF THE INVENTION

The present invention relates to a new and distinct variety of plant Toma-P, which bears fruit having the characteristics of both tomato and bell pepper. It can be produced and propagated asexually. The plant was produced by several stages of cross-breeding of Mexican, Indian, Hungarian, Dutch and Canadian paprika, Japanese tomatoes and Japanese peppers.

This cross-breeding has produced a new variety of tomato plant, Toma-P, with many of the characteristics of bell pepper. It is distinguished from its parents, as well as from the variety most similar to it, *Capsicum annuum*, by the nature of the fruit which has the texture of a bell pepper and the taste of a tomato.

DETAILED DESCRIPTION

A detailed description of this new variety is as follows, based upon observation made from plants and fruit grown in Japan.

Type: Determinate market: tomato.

Breeding: The invention plants are hybrids of Japanese tomato, Japanese sweet pepper and a strain of paprika native to Mexico, India, Hungary and Holland. The tomato plants were pollinated with paprika and are ultimately cross-pollinated with Japanese sweet pepper. The seeds are obtained by cultivating the parent plants in an open-pollinated greenhouse wherein bees are used as pollinators. The seeds are selected from those which have superior shapes and flavor when grown in a 2.5-acre (1 hectare) bed. The seeds of the invention plants have been deposited at the ATCC with Accession No. PTA-1824.

Propagation: Holds its distinguishing characteristics through succeeding propagation by grafting explants onto eggplants or onto tomato plants or by cultivating the growing buds individually.

DESCRIPTION OF THE PLANT

Habit: Suitable for use as a ground plant. It can be grown indoors or outdoors at a temperature of 15–40° C. When grown outdoors, the top should be cut after the plant reaches about one meter and tied down to the ground at an angle that follows the direction of the prevailing wind in order to prevent breakage of the stalks.

Growth: Can grow to a height of 4–5 meters.

Foliage: Leaves: At maturity, each plant has 100–120 leaves. The leaves are simple and are 300–400 cm². The leaves are spaced at approximately 10 cm as the internodal distance.

Main stems: Branches-about three branches from the main stem. 15–20 fruits grow on each branch at one time. The flowers are cross-shaped.

Fruit: Each plant contains about 30–60 fruits.

Characteristics of the Fruit: The fruit is a slightly flattened globe with prominent stem. It has an average weight of 100 grams–150 grams. The fruit is red when ripe, is firm and crunchy similar to an apple, and has no distinct smell. It has a sweet green pepper flavor somewhat similar to tomato or persimmon. The fruit has a waxy surface which becomes shiny when polished. Its outer skin is thin and easy to chew. Thus, it is slightly crunchy with central core bearing seeds.

Color: In the immature stage, the surface of the fruit is a uniform light green. At full growth, the color becomes whitish green. As it matures, it becomes purplish black, and finally when completely mature is a deep red.

Bearing Season: If grown from seed, fruit may be harvested about ninety days from when the seeds are planted, if the temperature is below 20° C. If the temperature is above 20° C., the fruits can be harvested about sixty days after planting of the seeds.

Disease Resistance: Generally sensitive to insects and to agricultural chemicals. Disease resistance is increased by growing at temperatures below 30° C., by regulating the amount of water provided, and by providing calcium. Specifically, the Toma-P of the invention is resistant to beto disease which causes stickiness, and eventually decomposition, of the leaves; to Anthracnose, wherein black spots appear on the surface of the leaf causing the leaf to blight; and to rinmon disease, in which brown crest-shaped patches appear on the surface of the leaf, causing the leaf to blight. The Toma-P of the invention is susceptible to gray mould (mildew) which occurs in a decayed flower and kills the stem; to sclerotinia stem rot which occurs in the stem and kills the entire plant; and to romicelli disease, wherein white patches spread on the back of the leaf, causing the leaf to whither. These appear to be the only plant diseases to which Toma-P is susceptible.

Use: Fruit can be marketed for human consumption.

Miscellaneous: The fruit has the flavor of tomatoes, but the general texture of bell pepper. When cut in half, the cross-section appears similar to that of bell pepper as shown in the drawings.

DEPOSIT INFORMATION

A deposit of the Toma-P seed of Triangle Associates, LLC, disclosed above and recited in the appended claims has been made with the American Type Culture Collection (ATCC), 10801 University Boulevard, Manassas, Va. 20110. The date of deposit was May 5, 2000. The deposit of 2,500 seeds were taken from the same deposit maintained by Triangle Associates, LLC since prior to the filing date of this application. All restrictions upon the deposit have been removed, and the deposit is intended to meet all the requirements of 37 C.F.R. §1.801–1.809. The ATCC accession number is PTA-1824. The deposit will be maintained in the depository for a period of 30 years, or 5 years after the last request, or for the effective life of the patent, whichever is longer, and will be replaced as necessary during that period.

What is claimed is:

1. A tomato seed designated Toma-P consisting of the hybridization product of Japanese tomatoes crossed with Japanese peppers and paprika, a sample of said seed having been deposited under ATCC Accession No. PTA-1824.

2. A tomato plant, or parts thereof, produced by growing the seed of claim 1.

3. Pollen of the plant of claim 2.

4. An ovule of the plant of claim 2.

5. A tomato plant, or parts thereof, having all of the physiological and morphological characteristics of the tomato plant of claim 2.

6. A tissue culture of regenerable cells of a tomato plant designated Toma-P, consisting of the hybridization product of Japanese tomatoes crossed with Japanese peppers and paprika, representative seed having been deposited under ATCC Accession No. PTA-1824, wherein the tissue regenerates plants capable of expressing all the morphological and physiological characteristics of the Toma-P line.

7. A tissue culture according to claim 6, the cells or protoplasts being from a tissue selected from the group consisting of leaves, pollen, embryos, roots, root tips, anthers, fruits and stems.

8. A tomato plant regenerated from the tissue culture of claim 6, capable of expressing all the morphological and physiological characteristics of Toma-P.

* * * * *